United States Patent
Sorenson

(10) Patent No.: US 12,220,503 B1
(45) Date of Patent: Feb. 11, 2025

(54) DECENTRALIZED AIRBORNE CONTAMINANT CAPTURE AND NEUTRALIZATION SYSTEM

(71) Applicant: Andrew Sorenson, Mobile, AL (US)

(72) Inventor: Andrew Sorenson, Mobile, AL (US)

(*) Notice: Subject to any disclaimer, the term of this patent is extended or adjusted under 35 U.S.C. 154(b) by 908 days.

(21) Appl. No.: 17/351,953

(22) Filed: Jun. 18, 2021

(51) Int. Cl.
*B01D 46/00* (2022.01)
*A61L 9/20* (2006.01)

(52) U.S. Cl.
CPC ............. *A61L 9/20* (2013.01); *B01D 46/0028* (2013.01); *A61L 2202/11* (2013.01); *A61L 2209/12* (2013.01); *A61L 2209/14* (2013.01); *B01D 2257/91* (2013.01); *B01D 2259/804* (2013.01)

(58) Field of Classification Search
CPC ............ B01D 46/0028; B01D 2257/91; B01D 2259/804; A61L 9/20; A61L 2202/11; A61L 2209/12; A61L 2209/14
USPC ....... 55/385.1, 470–473, 385.2, 418; 96/139; 131/233, 235.1, 242; 206/454, 710; 454/184, 187, 192
See application file for complete search history.

(56) References Cited

U.S. PATENT DOCUMENTS

| | | | | |
|---|---|---|---|---|
| 5,984,990 A | * | 11/1999 | McDonald | B25H 1/02 55/528 |
| 7,300,485 B1 | * | 11/2007 | Moore | B03C 3/30 131/233 |
| 7,335,244 B2 | * | 2/2008 | Kisakibaru | B01D 53/0407 454/192 |
| 7,419,533 B2 | * | 9/2008 | Son | B01D 46/12 55/482 |
| 7,591,867 B2 | * | 9/2009 | Choi | F24F 8/158 454/246 |
| 9,700,822 B2 | * | 7/2017 | Horng | B01D 46/62 |
| 10,610,817 B2 | * | 4/2020 | Swan | B01D 46/0043 |
| 10,694,682 B2 | | 6/2020 | Bogner et al. | |
| 10,806,099 B2 | | 10/2020 | Bogner et al. | |
| 2004/0192186 A1 | * | 9/2004 | Bourgeois | B01D 46/12 55/385.2 |
| 2008/0264257 A1 | * | 10/2008 | Ryder, III | F24F 8/00 29/411 |
| 2011/0100221 A1 | * | 5/2011 | Wu | B01D 46/12 96/64 |

FOREIGN PATENT DOCUMENTS

| | | | | |
|---|---|---|---|---|
| CN | 2509880 Y | * | 9/2002 | ............... A24B 3/10 |
| CN | 212016487 U | * | 11/2020 | ............. A62B 23/06 |
| EP | 2439456 A2 | | 4/2012 | |

* cited by examiner

*Primary Examiner* — Minh Chau T Pham
(74) *Attorney, Agent, or Firm* — AdamsIP, LLC; Stephen Thompson; J. Hunter Adams

(57) ABSTRACT

A decentralized multi-chamber air duct system for decontaminating air in indoor spaces is provided. The system includes an air duct having positive and negative pressure chambers each in fluid communication with a plenum chamber. A fan extracts air from an indoor space through the negative pressure chamber of the air duct into the plenum chamber, where the air is decontaminated before being discharged back into the same indoor space through the positive pressure chamber of the air duct.

19 Claims, 8 Drawing Sheets

DECENTRALIZED AIRBORNE CONTAMINANT CAPTURE AND NEUTRALIZATION SYSTEM

FIELD OF THE DISCLOSURE

The present disclosure relates generally to a decentralized multi-chamber air duct system for decontaminating air in occupied spaces.

BACKGROUND

Contagious airborne pathogens may linger in indoor air for as long as several hours, during which time occupants may breathe in airborne pathogens and become infected. The risk of transmission can be difficult to mitigate, particularly in public indoor spaces where occupants may remain for extended periods of time, such as workplaces, schools, churches, restaurants, hospitals, gyms, stores, movie theatres, or similar places. Risk may be mitigated through social distancing and/or masking, though these measures are not always practicable or even possible in some cases. For instance, wearing a mask at a gym during intensive exercising may be extremely uncomfortable for the mask wearer. In other cases, such as when eating or drinking, mask wearing becomes impossible.

Another manner of mitigating transmission risk is through the use of various types of air cleaning devices and/or by increasing air ventilation rates in indoor spaces. However, there are numerous drawbacks when implementing these types of mitigation efforts. Air cleaning devices installed to decontaminate air passing through existing ductwork may not be effective if the ventilation is not sufficient to turn over the air within an occupied space at a high rate. In turn, high ventilation rates often require costly equipment upgrades, especially in humid climates in which outdoor air brought into the occupied space to increase the ventilation rate may require dehumidification in order to prevent the growth of mold inside ductwork. Various types of standalone air cleaning devices are commercially available, but such devices typically draw air directly into the unit from a single location right at the unit and then return the decontaminated air at the same centralized location right at the unit, which may significantly limit the effectiveness of such units for decontaminating large indoor spaces. Additional units may be installed within an occupied space, but installing enough units to be reasonably effective may be cost prohibitive and may also clutter the occupied space.

Accordingly, a need exists in the art for an effective and inexpensive system for decontaminating indoor air.

SUMMARY

In one aspect, a decentralized multi-chamber air duct system for decontaminating air in occupied spaces and a method of using the system are provided. The system is designed to linearly capture, or extract, air from an indoor occupied space utilizing a multi-chamber air duct, remove or neutralize any contaminants present in the air, and then redistribute the decontaminated air linearly at low velocity back into the indoor space through the same air duct. The air duct comprises a single duct structure that is internally subdivided into the separate chambers, which may each extend lengthwise along the length of the air duct. The system captures and also redistributes the air in a linear manner along the length of the air duct so that the air capture and redistribution is decentralized from the decontamination equipment, which increases the ventilation rate of "clean" air and thus the efficiency of the system. Operating in this manner may reduce turbulent airflow patterns and reduce mixing of contaminated and clean air within the space. The system may be operated continuously in public indoor spaces to reduce the transmission of airborne pathogens by directly neutralizing such pathogens and increasing ventilation rates. The system may be a standalone system that is self-contained and thus does not require connection to any other HVAC (heating, ventilation, and air conditioning) systems or equipment to operate, but is still capable of decentralized air capture and redistribution.

In a preferred embodiment, the system comprises an air duct including a negative pressure chamber and a positive pressure chamber each disposed within the air duct. A wall of the negative pressure chamber has a plurality of intake openings through which the negative pressure chamber is in fluid communication with an exterior of the air duct, and a wall of the positive pressure chamber has a plurality of discharge openings through which the positive pressure chamber is in fluid communication with the exterior of the air duct. The air duct is positioned within an indoor space that is external to the air duct, preferably hanging from overhead supports in an elevated position above occupants of the indoor space. The system further comprises a plenum chamber that is in fluid communication with both the negative pressure chamber and the positive pressure chamber and is preferably disposed at one end of the air duct. The system further comprises a fan configured to draw air from the exterior of the air duct into the plenum chamber through the intake openings and the negative pressure chamber. The fan then discharges the air from the plenum chamber to the exterior of the air duct through the positive pressure chamber and the discharge openings. The system includes decontamination equipment housed inside the plenum chamber to decontaminate the air. The decontamination equipment preferably includes at least an air filter that the air drawn into the plenum chamber passes through before being discharged through the positive pressure chamber of the air duct. Other decontamination equipment may optionally include UV-C lamps or a bipolar ionizer, either of which may be utilized separately or in combination with each other or with the air filter.

In a preferred embodiment, the air duct is elongated and has a bottom wall, a top wall, two opposing side walls, and two opposing ends. The air duct preferably includes two opposing positive pressure chambers. The positive pressure chambers are each disposed within the air duct lengthwise along one of the two respective opposing side walls of the air duct, and the negative pressure chamber is disposed lengthwise within the air duct between the two positive pressure chambers. The bottom wall of the air duct has a plurality of intake openings through which the negative pressure chamber is in fluid communication with an exterior of the air duct, and each of the side walls of the air duct has a plurality of discharge openings through which the opposing positive pressure chambers are each in fluid communication with the exterior of the air duct. The plenum chamber is disposed at one end of the air duct and is in fluid communication individually with the negative pressure chamber and with both of the positive pressure chambers. The fan is disposed within the plenum chamber, and when the fan is activated it draws air into the plenum chamber from the exterior of the air duct through the intake openings and the negative pressure chamber. Thus, air to be decontaminated is drawn directly from the indoor space from the bottom of the air duct, which is generally directly above occupants of the indoor space. The fan then discharges the air from the plenum chamber to the exterior of the air duct through the opposing positive pressure chambers and the discharge openings. Thus, the clean air is redistributed back into the indoor space from the sides of the air duct along the length of the air duct. The longitudinal configuration of the individual chambers of the air duct provides effective low velocity, laminar redistribution of decontaminated air back into the occupied space at a high ventilation rate.

In a preferred embodiment, the duct may be made of a pliable fabric material held in tension by elongated tracks, which are preferably retained in a rectangular relation to each other by horizontal and vertical spacers attached to each of the tracks so that the fabric duct has a generally rectangular shape. The fabric duct may have four corners each longitudinally secured to a rod by a loop attached to the air duct at each corner of the air duct and extending longitudinally along a length of the corner. The loop is positioned longitudinally around one of the rods, and each rod may be retained in longitudinal relation with one respective track by slidably inserting the rod into a longitudinal groove of the track. The groove has an open side that extends longitudinally along the length of the track. The open end has a diameter that is smaller than the diameter of the rod, which allows each rod to be slidably inserted into one of the tracks and retained in place within the groove. The open side of the groove allows a portion of the fabric to extend through the open side so that the rod can be inserted into the groove with the fabric looped around the rod. The system preferably includes vertical and longitudinal tensioners to hold the fabric in tension.

In an alternative embodiment, the system may be used to draw air from an outdoor space that is separate from the indoor space in which the air duct is disposed and to discharge the outdoor air into the indoor occupied space while simultaneously extracting indoor air and discharging the indoor air into the outdoor space, thereby increasing the ventilation rate by utilizing outdoor air to replace indoor air. In this embodiment, the system comprises a fan box that includes an extraction plenum chamber in fluid communication with the negative pressure chamber and a separate discharge plenum chamber in fluid communication with the positive pressure chamber. The extraction plenum chamber of the fan box is in fluid communication with the outdoor space through an outlet duct, and the discharge plenum chamber is in fluid communication with the outdoor space through an inlet duct. Air from the indoor space is extracted through the intake openings of the negative pressure chamber by a first fan disposed in the extraction plenum chamber and then discharged to the outdoor space through the outlet duct. Air from the outdoor space is drawn into the discharge plenum chamber from the outdoor space by a second fan through the inlet duct and then discharged into the indoor space through the discharge openings of the positive pressure chamber.

The foregoing summary has outlined some features of the system and method of the present disclosure so that those skilled in the pertinent art may better understand the detailed description that follows. Additional features that form the subject of the claims will be described hereinafter. Those skilled in the pertinent art should appreciate that they can readily utilize these features for designing or modifying other structures for carrying out the same purpose of the system and method disclosed herein. Those skilled in the pertinent art should also realize that such equivalent designs or modifications do not depart from the scope of the system and method of the present disclosure.

DESCRIPTION OF THE DRAWINGS

These and other features, aspects, and advantages of the present disclosure will become better understood with regard to the following description, appended claims, and accompanying drawings where:

DETAILED DESCRIPTION

Figure 1:
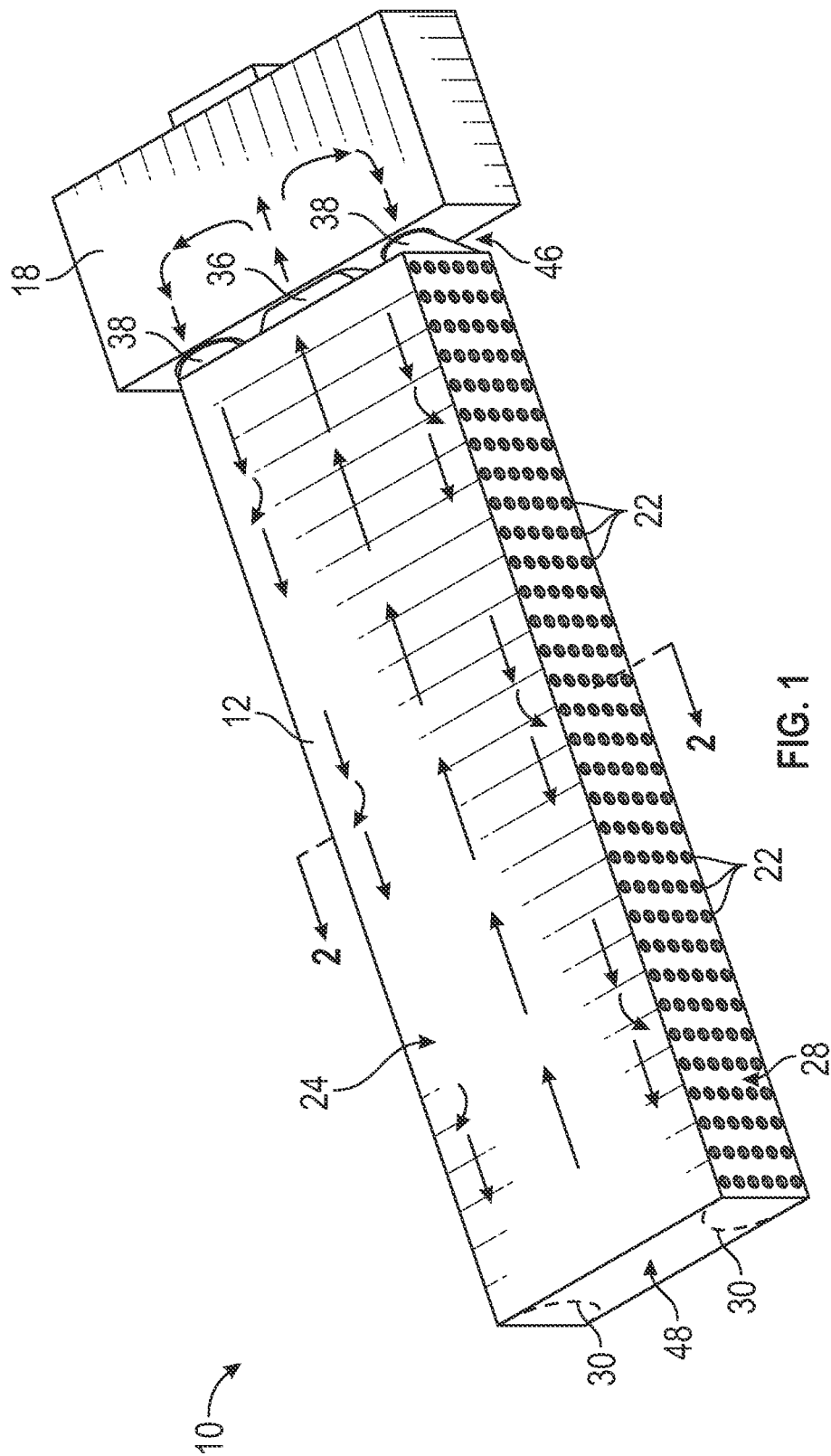
FIG. 1 is a perspective view of a multi-chamber air duct system in accordance with the present disclosure.

In the Summary above and in this Detailed Description, and the claims below, and in the accompanying drawings, reference is made to particular features, including method steps, of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with/or in the context of other particular aspects of the embodiments of the invention, and in the invention generally.

The term "comprises" and grammatical equivalents thereof are used herein to mean that other components, steps, etc. are optionally present. For example, a system "comprising" components A, B, and C can contain only components A, B, and C, or can contain not only components A, B, and C, but also one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

A decentralized multi-chamber air duct system 10 for decontaminating air in indoor spaces and a method of using the system are provided. The system 10 comprises a multi-chamber air duct 12 that is internally subdivided into separate chambers 14, 16, each of which is individually in fluid communication with a plenum chamber 18. Each of the separate chambers 14, 16 are contained within a single duct structure 12, and each of the separate chambers 14, 16 preferably extend lengthwise along the entire length of the air duct 12. The air duct 12 may be installed within an indoor space, preferably hanging from overhead supports in an elevated position above an area where occupants of the indoor space would be. The multi-chamber duct 12 may extract indoor air from directly above the occupants through one chamber, capture or neutralize any contaminants present in the air, and then discharge the "clean" air directly back into the indoor space above the occupants through a different chamber of the same duct structure. In a preferred embodiment, the air duct 12 is elongated and has a generally rectangular cross-sectional shape having a top wall 24, a bottom wall 26, and two opposing side walls 28. The internal chambers 14, 16 are separated by internal walls 30 and are not directly in fluid communication with each other, meaning that air cannot flow directly between the internal chambers 14, 16 (though each internal chamber 14, 16 is individually in fluid communication with the plenum chamber 18 and with the space surrounding the duct structure 12). The air duct 12 has two opposing ends 46, 48 and preferably extends in a straight line between the opposing ends, although the duct 12 may alternatively bend or may be angled in order to provide a customized fit within a particular indoor room. In other alternative embodiments, the air duct 12 may optionally have curved sections or various other shapes for aesthetic purposes. The plenum chamber 18 is connected to one end 48 of the air duct 12. The system 10 is designed to extract indoor air along the length of the duct 12 between the opposing ends 46, 48 and to also discharge clean air along the length of the duct 12.

The air duct 12 may be constructed of any suitable material, which may include rigid materials, such as metal or plastic, or pliable materials such as fabric, which may include woven or non-woven fabrics. FIGS. 1-4 illustrate an air duct 12 constructed of a rigid material, and FIGS. 5-9 illustrate an air duct 50 constructed of pliable fabric, which is preferably polyester fabric. The air duct 12 includes a negative pressure chamber 14 and a positive pressure chamber 16, each of which is disposed within the air duct 12. A wall 26 of the negative pressure chamber 14 has a plurality of intake openings 20 through which the negative pressure chamber 14 is in fluid communication with an exterior of the air duct 12, which is the indoor space in which the duct 12 is installed and from which air is extracted for decontamination. Thus, the exterior of the air duct 12 is the open space surrounding the external walls 24, 26, 28 of the air duct 12 along the length of the air duct 12. A wall 28 of the positive pressure chamber 16 has a plurality of discharge openings 22 through which the positive pressure chamber 16 is in fluid communication with the exterior of the air duct 12. The wall 28 of the positive pressure chamber 16 that has the discharge openings 22 is defined by an external wall of the duct structure 12. Likewise, the wall 26 of the negative pressure chamber 14 that has the intake openings 20 is also defined by an external wall of the duct structure 12. The external walls of the duct structure 12 may include the top wall 24, bottom wall 26, and/or side walls 28 of a rectangular duct 12 or similarly positioned external walls of a duct having a different cross-sectional shape.

Figure 2:
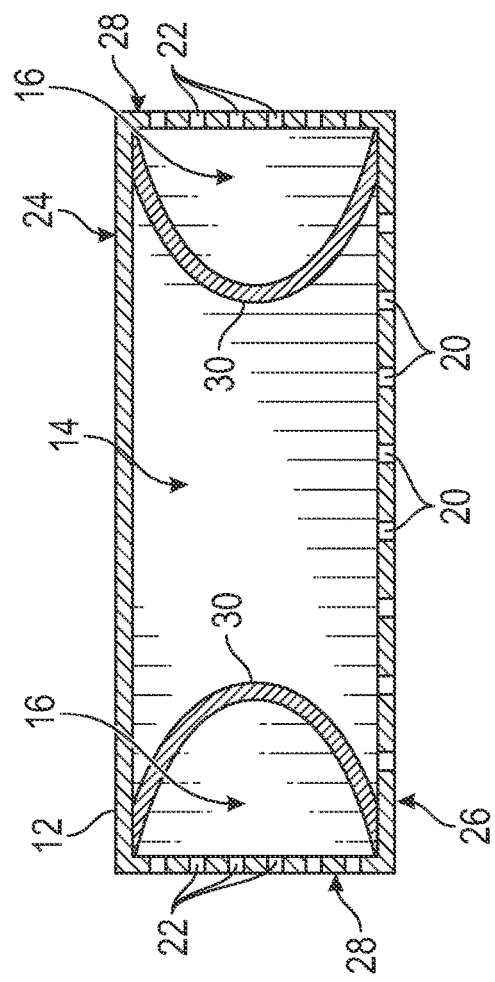
FIG. 2 is a cross-sectional view of a duct of the multi-chamber air duct system shown in FIG. 1.
Figure 3:
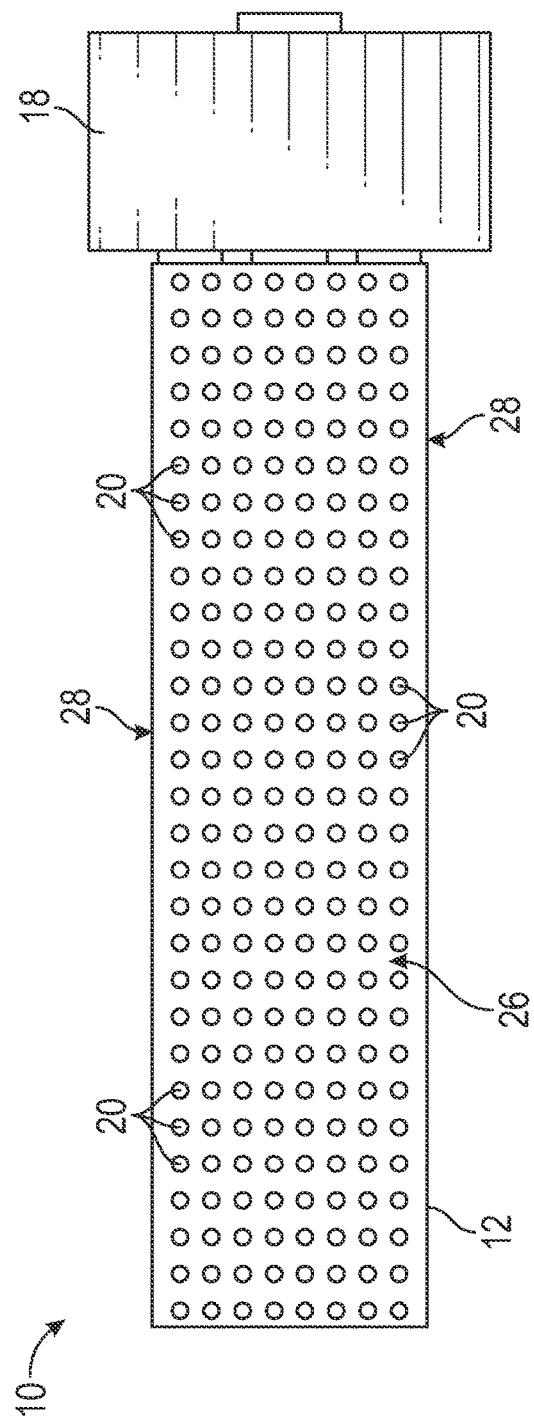
FIG. 3 is a bottom plan view of a multi-chamber air duct system in accordance with the present disclosure.

In a preferred embodiment, the air duct 12 includes two opposing positive pressure chambers 16. As best seen in FIGS. 1 and 2, the positive pressure chambers 16 are each disposed within the air duct 12 lengthwise along one of the two respective opposing side walls 28 of the air duct 12, and the negative pressure chamber 14 is disposed lengthwise within the air duct 12 between the two positive pressure chambers 16. Each of the positive pressure chambers 16 is separated from the negative pressure chamber 14 by an internal wall 30. In a preferred embodiment, as best seen in FIG. 2, the internal wall 30 is a curved wall that is attached to an interior of the air duct structure 12 at an upper corner and at an adjacent lower corner of the duct 12. Thus, each positive pressure chamber 16 is preferably defined by one internal wall 30 and all or substantially all of one side wall 28. Similarly, the negative pressure chamber 14 is preferably defined by the two opposing internal walls 30 and all or substantially all of both the top wall 24 and the bottom wall 26 of the duct 12. The bottom wall 26 of the air duct 12 has a plurality of intake openings 20 through which air may be extracted from the indoor space into the negative pressure chamber 14, and each of the side walls 28 of the air duct 12 has a plurality of discharge openings 22 through which decontaminated air may be discharged into the indoor space from each of the positive pressure chambers 16. Because the intake 20 and discharge 22 openings are distributed throughout walls 26 and 28 along the length of the duct 12, as best seen in FIGS. 1 and 3, the system 10 allows the air duct 12 to linearly extract air from the indoor space and simultaneously to linearly redistribute decontaminated air at low velocity back into the indoor space utilizing the entire length of the same air duct structure 12. This arrangement allows for effective air decontamination at high ventilation rates.

Figure 4:
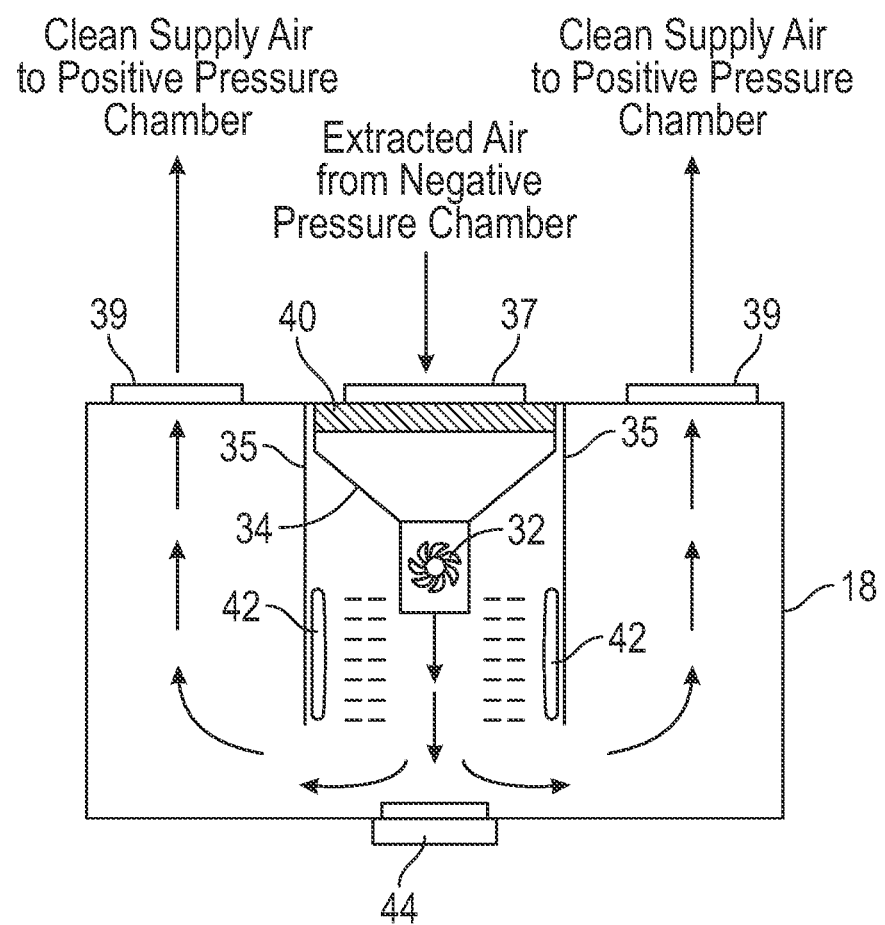
FIG. 4 is a schematic view of an interior of a plenum chamber of a multi-chamber air duct system in accordance with the present disclosure.

Both of the positive pressure chambers 16 and the negative pressure chamber 14 are each individually in fluid communication with the plenum chamber 18, as best seen in FIG. 1. The system 10 further comprises a fan 32 configured to draw air from the exterior of the air duct 12 into the plenum chamber 18 through the intake openings 20 on the bottom wall 26 of the duct 12. The air is drawn into the negative pressure chamber 14 and then into the plenum chamber 18. FIG. 4 shows a schematic view of the interior of the plenum chamber 18. The arrows shown in FIG. 4 indicate the direction of airflow within the plenum chamber 18, which is directed from the negative pressure chamber, which has a slight negative pressure due to the suction of the fan 32, into the positive pressure chambers 16, which each have a slight positive pressure due to the discharge pressure of the fan 32. The interior of the plenum chamber 18 preferably has internal walls 35 positioned in an arrangement that aids in directing the air from the fan 32 discharge into the positive pressure chambers 16 of the air duct 12. The system 10 includes decontamination equipment housed inside the plenum chamber 18 to decontaminate the air as it passes into and through the plenum chamber 18. Thus, the fan 32 discharges decontaminated air from the plenum chamber 18 directly into each of the positive pressure chambers 16. The decontaminated air is then discharged to the exterior of the air duct 12 through the discharge openings 22 on each of the side walls 28 of the air duct 12.

The decontamination equipment housed in the plenum chamber 18 preferably includes at least an air filter 40, which is preferably a HEPA (high-efficiency particulate air) filter. The fan 32 forces the air from the negative pressure chamber 14 to pass through the filter 40 before being discharged back into the indoor space through the discharge openings 22. The fan 32 is preferably arranged inline with the negative pressure chamber 14 to facilitate efficient air extraction. The fan 32 may be disposed within a fan box having walls 34 that funnel the air through the fan 32 blades to maximize efficiency. As seen in FIG. 4, the filter 40 preferably covers an inlet 37 of the plenum chamber 18 to ensure that all of the air extracted through the negative pressure chamber 18 passes through the filter 40. As shown in FIG. 4, the system 10 may optionally include UV-C lamps 42 and/or a bipolar ionizer 44 for additional decontamination capability. In a preferred embodiment, two opposing UV-C lamps 42 may be installed downstream of the filter 40 on an inside of each of the internal walls 35 of the plenum chamber 18 and facing inwardly. The UV-C lamps 42 are disposed within the enclosed space of the plenum chamber and are positioned so that all of the air that passes through the filter 40 is exposed to the UV light emitted by the lamps 42 to inactivate any airborne pathogens and/or microorganisms such as viruses, bacteria, or mold. In addition, a bipolar ionizer 44 may preferably be installed on a back wall of the plenum chamber 18 to disperse ions throughout the plenum chamber 18 to further deactivate any remaining pathogens present in the air that is discharged through the positive pressure chambers 16. The filter 40, UV-C lamps 42, and bipolar ionizer 44 may each be utilized individually for air decontamination or in any combination. In a preferred embodiment, the system 10 may utilize all three in combination.

As best seen in FIG. 4, the plenum chamber 18 may have an inlet flange or fitting 37 extending outwardly for connecting the negative pressure chamber 14 to the plenum chamber 18 and two outlet fittings 39 for connecting each of the positive pressure chambers 16 to the plenum chamber 18. As shown in FIG. 1, the air duct 12 may have a connector 36 sized and shaped so that the connector 36 securely fits onto inlet fitting 37 to connect the negative pressure chamber 14 to the plenum chamber 18. Similarly, the air duct 12 may have two opposing connectors 38 each sized and shaped so that the connectors 38 securely fit onto each outlet fitting 39 to connect each of the positive pressure chambers 16 to the plenum chamber 18. As shown in FIG. 1, the plenum chamber 18 is preferably installed directly adjacent to one end 48 of the air duct 12 by connectors 36 and 38. Alternatively, the plenum chamber 18 may be installed in a different location within the room or even in a separate room, and suitable ductwork may be used to connect the connectors 36, 38 of the air duct 12 to the fittings 37, 39 of the plenum chamber 18. This type of installation may be utilized to conceal the plenum chamber 18 for aesthetic purposes or to minimize the sound of the fan 32 for occupants of the space.

To use the system 10 to capture and/or neutralize airborne contaminants, the system 10 is installed within an indoor space from which air is to be extracted for decontamination and redistribution. The air duct 12 is preferably installed so that it is hanging from overhead supports in an elevated position above an area of the indoor space where occupants of the space are likely to be. The plenum chamber 18 is preferably installed directly adjacent to the air duct 12, as shown in FIG. 1, and may also hang from overhead supports or may otherwise be connected to an overhead structure. Any suitable hardware for hanging air ducts may be utilized. The fan 32 may then be activated to create suction in the negative pressure chamber 14 to draw air into the negative pressure chamber 14 from the interior of the room through the intake openings 20. Thus, air to be decontaminated is drawn directly from the indoor space from the bottom side 26 of the air duct 12, which is generally directly above occupants of the indoor space. The fan 32 forces the air from the negative pressure chamber 14 into the plenum chamber 18, where the air is treated by decontamination equipment, which may include the HEPA filter 40, UV-C lamps 42, and/or the bipolar ionizer 44. The fan 32 then discharges the cleaned air from the plenum chamber 18 into the positive pressure chambers 16, which redistributes the cleaned air back into the indoor space through the discharge openings 22. The clean air is preferably redistributed from the sides 28 of the air duct 12 along the length of the air duct 12. By extracting and redistributing air linearly along the length of the air duct 12, the air capture and redistribution is decentralized from the decontamination equipment, which allows the system 10 to provide effective low velocity, laminar redistribution of decontaminated air back into the occupied space at a high ventilation rate. Operating in this manner may reduce turbulent airflow patterns and reduce mixing of contaminated and clean air within the space. The system may be operated continuously in public indoor spaces to reduce the transmission of airborne pathogens by directly neutralizing such pathogens and increasing ventilation rates.

Figure 5:
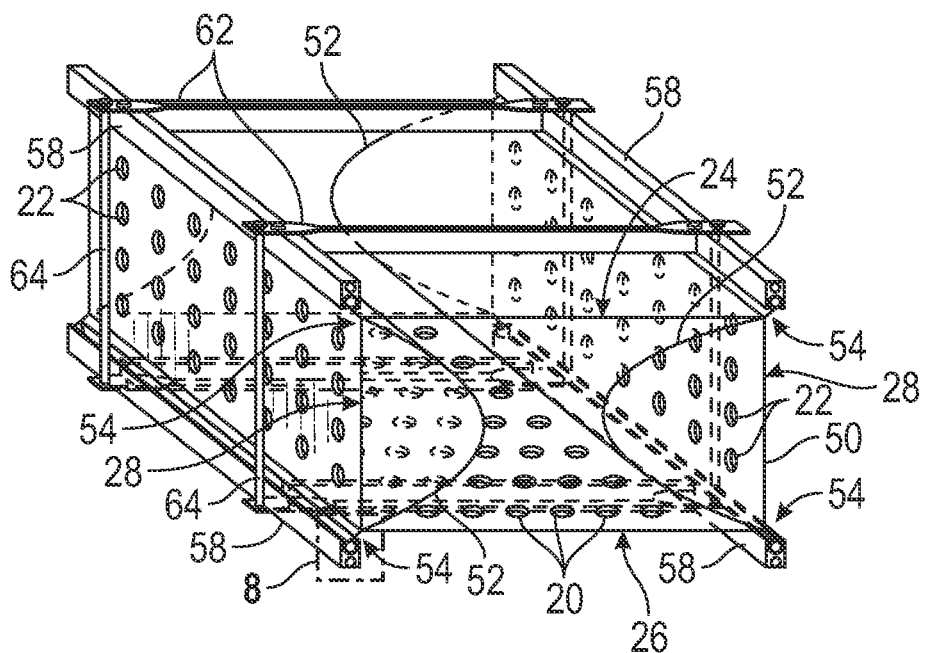
FIG. 5 is a perspective view of a multi-chamber air duct system with a duct made of a pliable fabric in accordance with the present disclosure.
Figure 6:
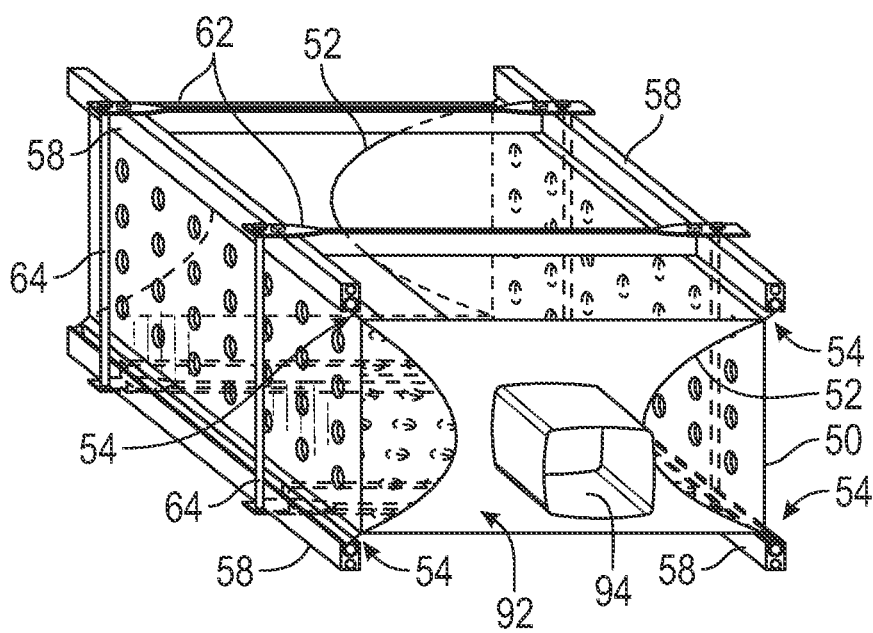
FIG. 6 is a perspective view of a multi-chamber air duct system with a duct made of a pliable fabric in accordance with the present disclosure.
Figure 7:
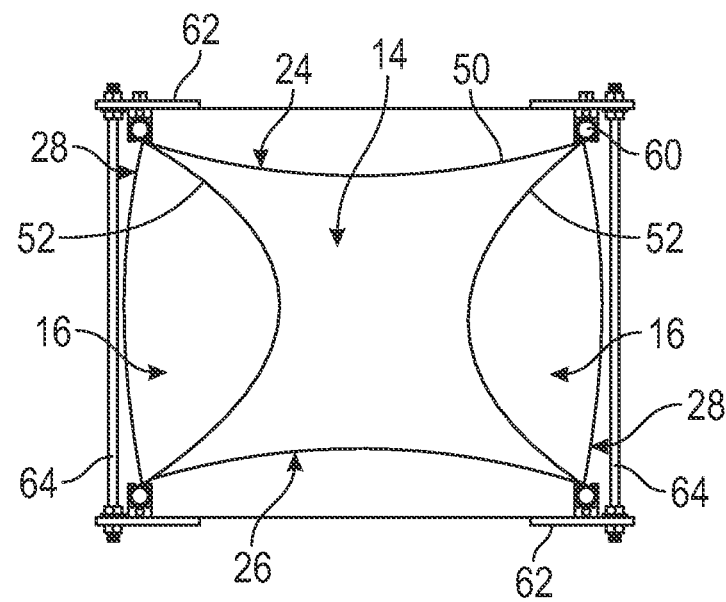
FIG. 7 is a cross-sectional view of the duct made of pliable fabric shown in FIG. 5.
Figure 8:
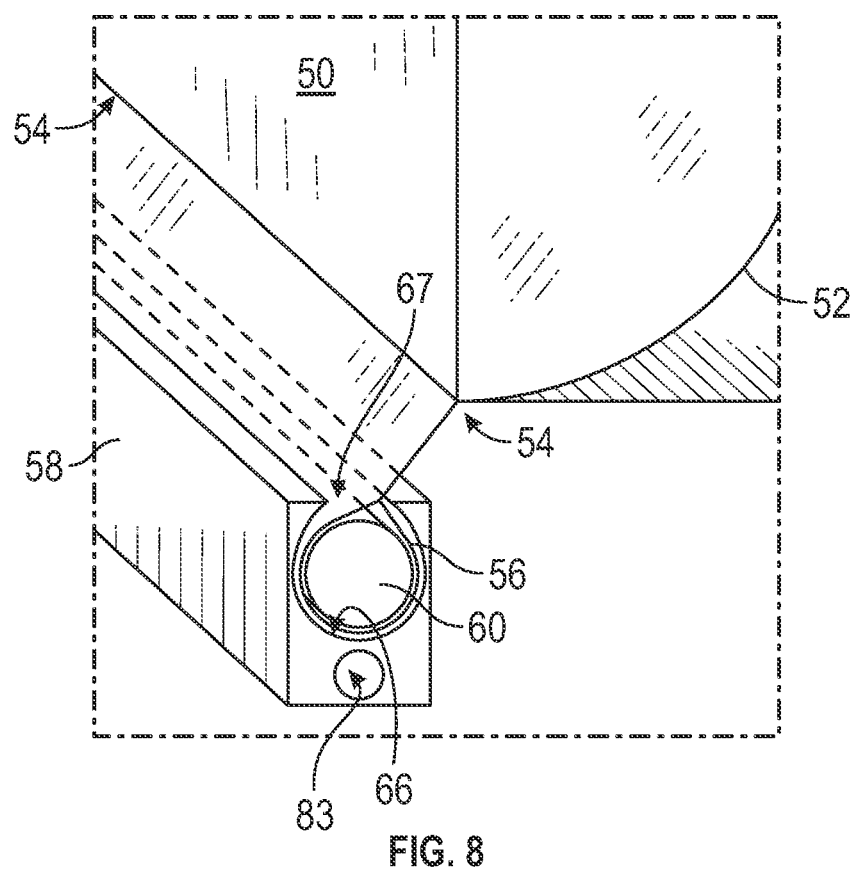
FIG. 8 is a partial perspective view of an attachment point of a fabric multi-chamber air duct to a track system in accordance with the present disclosure.

In a preferred embodiment, as best seen in FIGS. 5-7, the air duct 50 may be made of a pliable fabric, which is preferably polyester fabric. In this embodiment, the fabric material may be held in tension by a set of elongated tracks 58 retained in a spaced relation to each other to define the general shape and positioning of the duct. Preferably, the system 10 comprises four tracks 58, which are preferably retained in a rectangular relation to each other by horizontal and vertical spacers 62, 64 attached to each of the tracks 58, as shown in FIG. 5, which shows a cross-section of the duct 50 and tracks 58. As best seen in FIG. 8, which illustrates a connection of one corner 54 of the duct 50 to one of the tracks 58, each track 58 has a longitudinal groove 66 that extends along a length of the track 58. Each groove 66 has an open side 67 that also extends longitudinally along the length of the track 58 and may be defined by a profiled surface extending the length of the track 58. The system 10 further comprises four elongated rods 60 that may each be slidably inserted into each respective groove 66 of one of the tracks 58. The open end 67 of each groove 66 has a diameter that is smaller than the diameter of the rod 60, which allows each rod 60 to be retained in place after the rod 60 has been inserted into a groove 66.

The fabric duct 50 is preferably tensioned so that it has a generally rectangular shape including four corners 54, which include two upper corners at an intersection of a top wall 24 and a side wall 28 and two lower corners at an intersection of a bottom wall 26 and a side wall 28. In a preferred embodiment, the fabric duct 50 includes a loop 56 sewn into the fabric duct 50 at each corner 54 and extending longitudinally along a length of each corner 54, as best seen in FIG. 8. To secure the fabric duct 50 to the tracks 58, each corner 54 may be longitudinally secured to a rod 60 by inserting the rod 60 into the loop 56 attached to that corner 54. Each rod 60 may then be by slidably inserted into the longitudinal groove 66 of one of the tracks 58 with the loop 56 surrounding the rod 60, which retains both the rod 60 and a corner 54 of the duct 50 in longitudinal relation with one respective track 58. The open side 67 of the groove 66 allows a portion of the fabric to extend through the open side 67 so that the rod 60 can be inserted into the groove 66 with the fabric looped around the rod 60.

The tracks 58 may be retained in a spaced relation to each other by both horizontal spacing elements 62 and vertical spacing elements 64, as best seen in FIG. 5. The horizontal spacing elements 62 may each be fastened to two upper tracks 58 or to two lower tracks 58 to maintain each of the upper and lower tracks 58 at a defined horizontal distance apart from each other. In a preferred embodiment, the horizontal spacing elements 62 have a defined length designed to be utilized with a fabric duct 50 of a defined size so that the horizontal spacing between tracks 58 is not adjustable. The vertical spacing between tracks 58 is preferably adjustable, and the vertical spacing elements 64 may function as vertical tensioners. In a preferred embodiment, the horizontal spacing elements 62 have openings at opposing ends through which the vertical spacing elements 64 may be inserted. The vertical spacing elements 64 may have at least one threaded end to facilitate vertical adjustment. As best seen in FIG. 7, threaded fasteners may be utilized with the threaded vertical spacing element 64, or at least one of the openings in one of the horizontal spacing elements 62 may have compatible threads, so that the vertical spacing elements 64 and/or fasteners may be rotated to adjust the vertical spacing between the tracks 58, which may be adjusted to adjust the tension of the fabric duct 50.

Figure 9A:
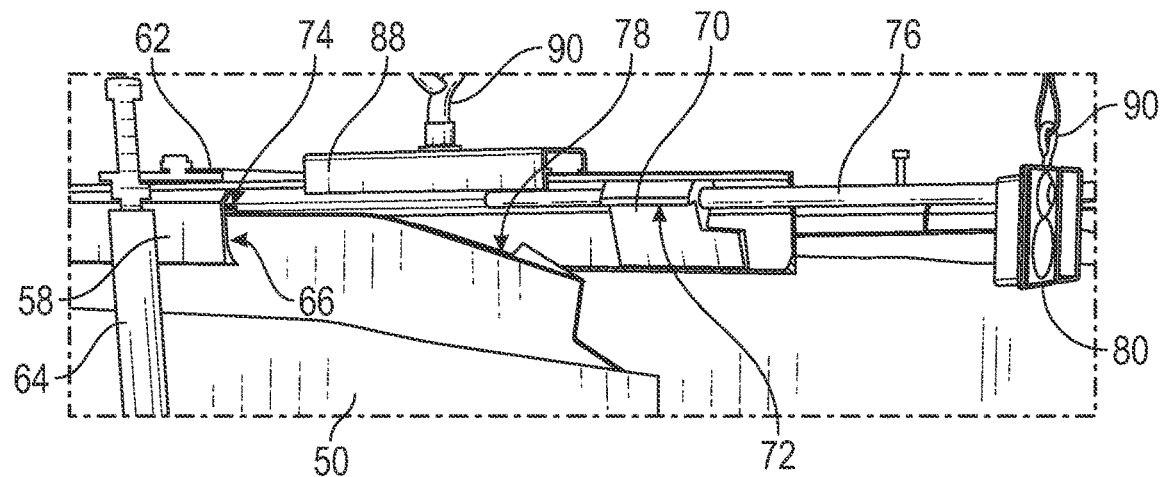
FIG. 9A is a perspective view of a tensioning system for a fabric multi-chamber air duct in accordance with the present disclosure.
Figure 9B:
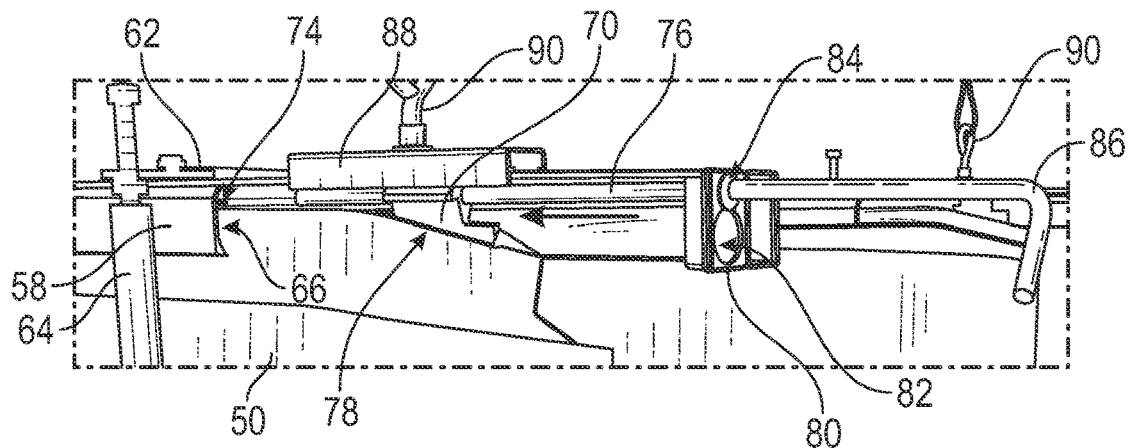
FIG. 9B is a perspective view of a tensioning system for a fabric multi-chamber air duct in accordance with the present disclosure.
Figure 9C:
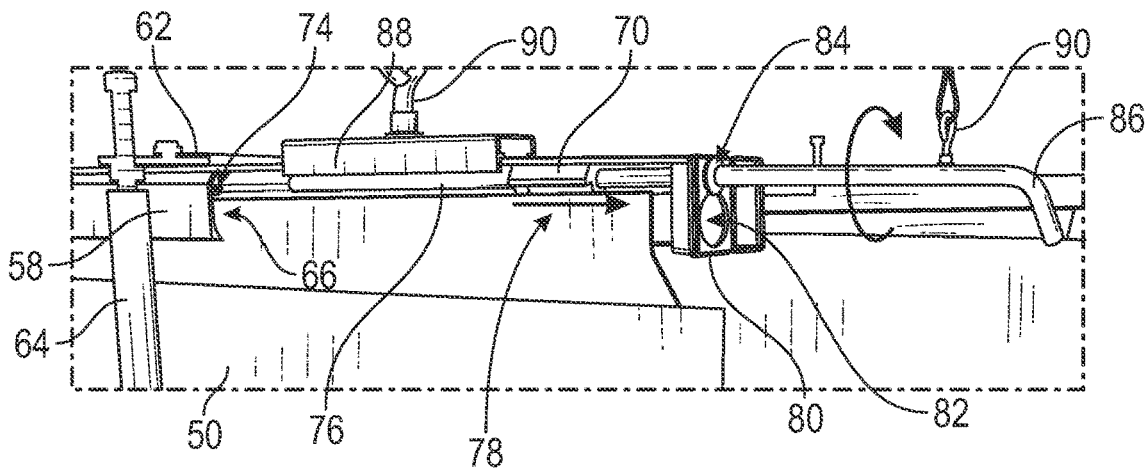
FIG. 9C is a perspective view of a tensioning system for a fabric multi-chamber air duct in accordance with the present disclosure.

In a preferred embodiment, the system 10 also includes longitudinal tensioners to hold the fabric in tension longitudinally to ensure that the fabric duct 50 does not slide along the rods 60 during normal use due to airflow and changes in pressure within the air duct 50. FIGS. 9A-9C illustrate the longitudinal tensioners. In each of FIGS. 9A-9C, a portion of an upper track 58 is shown as being removed so that the interior of the track 58 is visible. In this embodiment, the fabric duct 50 preferably has an open pocket 78 sewn onto an end of each loop 56 of the fabric duct 50 to provide an attachment point for a tensioning element 70. In a preferred embodiment, the tensioning element 70 has a threaded opening through which a threaded rod 76 is installed so that the tensioning element 70 will move longitudinally along a length of the rod 76 when the rod 76 is rotated while the rod 76 is retained in a longitudinally fixed position and the tensioning element 70 is retained in a rotationally fixed position.

In each of FIGS. 9A-9C, a rod 60 surrounded by one of the loops 56 has already been fully inserted into a groove 66 of one of the tracks 58 with the pocket 78 extending loosely past the end of the rod 60. In a preferred embodiment, the tensioning element 70 may have two opposing edges 72 extending outwardly, and the interior of each track 58 may have interior grooved surfaces 74 having the same cross-sectional shape of the edges 72 of the tensioning element 70 so that the tensioning element 70 can slide within the track 58 along the grooved surfaces 74. The grooved surfaces 74 also do not allow the tensioning element 70 to rotate. To provide longitudinal tensioning to the fabric duct 50, the pocket 78 portion of the fabric of the duct may be pulled down slightly through the open end 67 of the groove 66 of the track, and the tensioning element 70 with the threaded rod 76 may be inserted into the grooved surfaces 74 of the track 58, as shown in FIG. 9A. A cap 80 may be utilized to cap an end of the track 58. The threaded rod 76 may have a head 84 held in place by the cap 80 once installed. As shown in FIG. 9B, the threaded rod 76 and tensioning element 70 may be inserted until the tensioning element 70 is positioned adjacent to the pocket 78 of the fabric, at which point the fabric may be adjusted so that the pocket 78 is looped around and covering the tensioning element 70. FIG. 9C shows the pocket 78 completely surrounding the tensioning element 70, at which point the fabric duct 50 may be tensioned. To tension the fabric, the tensioning element 70 may be forced outward by engaging the head 84 of the threaded rod 76 with a wrench 86 and rotating the wrench 86, as shown in FIG. 9C. This action will slide the tensioning element 70 within the track 58 in an outward direction toward the cap 80, which causes the tensioning element 70 to engage with the pocket 78 and pull on the fabric of the duct 50, thereby causing the fabric duct 50 to become tensioned in a longitudinal direction. Another tensioner may be used on an opposite end of the fabric duct 50 to keep the duct tensioned from both ends. The cap 80 may have an opening 82 aligned with the groove 66 of each of the tracks 58. The grooved surfaces 74 of each track 58 may extend only a distance from an end of the track 58 sufficient to accommodate the tensioning element 70, and each track 58 may also have a smaller opening 83 to accommodate an end of the threaded rod 76. In a preferred embodiment, the upper track 58 may have a bracket 88 slidably secured to the track 58, as shown in FIGS. 9A-9C. Hanging hooks 90 or other types of attachment points for hanging the duct 50 may be attached to the brackets 88 to facilitate installation of the duct 50 in an overhead position suspended from a ceiling or other overhead structure.

The fabric duct 50 may have intake openings 20 and discharges openings 22 formed within the fabric for air intake and discharge as previously described. Alternatively, the side walls 28 and the bottom wall 26 of the fabric duct 50 may be made of a fabric that allows suction and discharge of air through the fabric without the need for defined openings formed within the fabric. As used herein, "intake openings" and "discharge openings" may include openings in fabric that allow suction and discharge of air through the fabric. The fabric duct 50 also has a negative pressure chamber 14 and a positive pressure chamber 16, and preferably two opposing positive pressure chambers 16, as best seen in FIG. 5. The air duct chambers 14, 16 are individually in fluid communication with the plenum chamber 18. The positive 16 and negative 14 pressure chambers are separated by internal walls 52, which are preferably also made of pliable fabric. The fabric of the internal walls 52 is preferably a thicker fabric material that substantially prevents any direct transfer of air from the positive pressure chambers 16 into the negative pressure chamber 14 through the internal walls 52. Similarly, the top wall 24 is preferably also made of a thicker fabric so that most or substantially all of the air intake into the negative pressure chamber is through the bottom wall 26, which is generally positioned directly over occupants of the indoor space. The fabric of the internal walls 52 may preferably be sewn into the corners 54 of the fabric duct 50 to attach the internal separation walls 52 to the duct 50 to form the positive 16 and negative 14 pressure chambers. FIG. 5 shows the internal walls 52 in the general shape that they would be in when the system 10 is in use, though the walls 52 are pliable and would not retain this shape when the system 10 is not in use. FIG. 7 illustrates a cross-sectional view of the fabric duct 50 when the system 10 is in use, which shows a slight deformation of the fabric duct 50 and internal walls 52 due to differences in pressure between the positive pressure chambers 16 and the negative pressure chamber 14.

Figure 10:
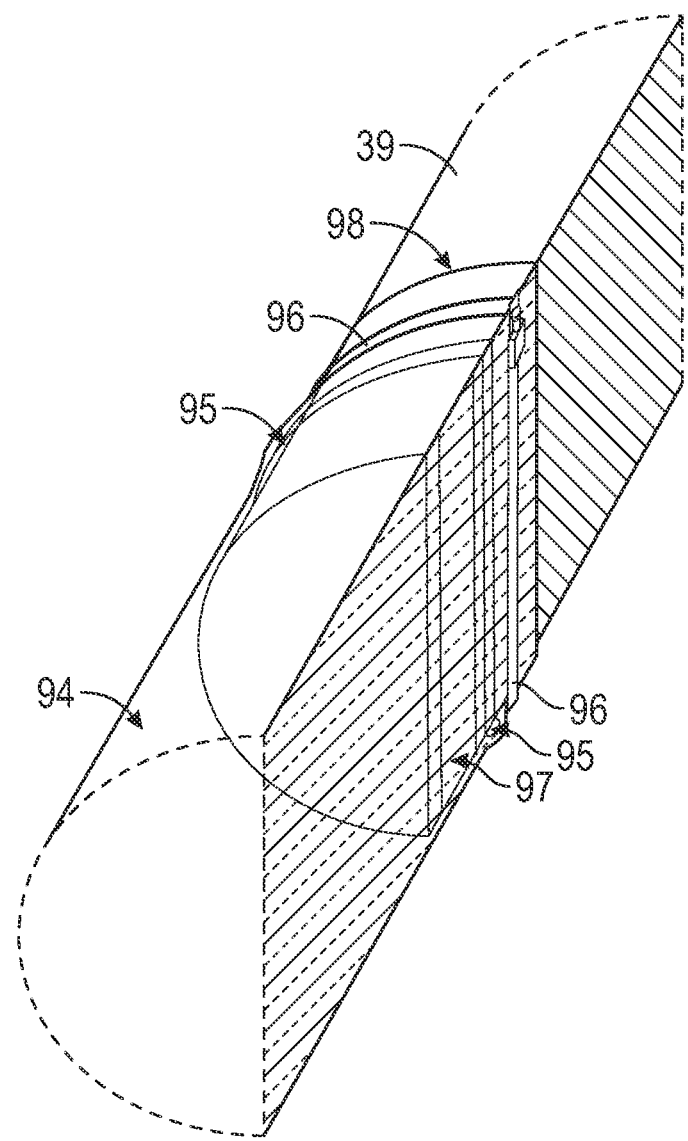
FIG. 10 is a perspective view of a connector for connecting a fabric air duct to a rigid inlet fitting in accordance with the present disclosure.

FIG. 6 shows an end of the fabric duct 50 to which the air duct chambers 14 and 16 may be connected to the plenum chamber 18. The plenum chamber 18 shown in FIGS. 1 and 4 may also be utilized with the fabric duct 50. FIG. 10 illustrates one preferred embodiment of a connection between the positive pressure chambers 16 and the outlet fittings 39 of the plenum chamber 18, which may have a semicircular shape to generally match the shape of the positive pressure chambers 16. A similar connection may be utilized to connect the negative pressure chamber 14 to the inlet fitting 37 of the plenum chamber 18, though this fitting 37 preferably has a rectangular or circular shape. As shown in FIG. 6, the fabric duct 50 may have an end wall 92 sewn onto the edges of the top wall 24, the bottom wall 26, and the internal walls 52. A central opening may be formed in the end wall for connection to the inlet fitting 37, and openings may remain to allow access to the positive pressure chambers 16 for connection to the outlet fittings 39. As shown in FIG. 6, a fabric extension 94 may be sewn onto the end of the central opening for connection to fitting 37. Although FIG. 6 shows an extension 94 only on the central opening to the negative pressure chamber 14, extensions may also be sewn onto the open end of each positive pressure chamber 16 for connection to fittings 39. FIG. 10 illustrates a generally semicircular fabric extension 94 connected to fitting 39. In a preferred embodiment, the fittings 37, 39 each have a lip 95 or flange around which the fabric extensions 94 may be positioned so that an end 98 of the fabric extension 94 extends past the lip 95, as shown in FIG. 10. A clamp 96, which is preferably strap that can be tightened, may then be placed over the fabric extensions 94 around each of the fittings 37 and 39 between the lip 95 and the end 98 of the fabric extension 94. The clamp 96 may then be tightened to secure each of the extensions 94 to the rigid fittings 37 and 39. A hook and loop type fastener 97 may optionally be adhered to the rigid fitting 37, 39 to help secure the extension 94 to the fitting and act as a seal. In an alternative embodiment, the fabric extensions 94 may be clamped onto a flange, which may then be bolted onto a flange of the plenum chamber 18, or may be placed between flanges before bolting the flanges together to secure the fabric in place. Other suitable types of connections may also be utilized and still fall within the scope of the present disclosure.

Figure 11:
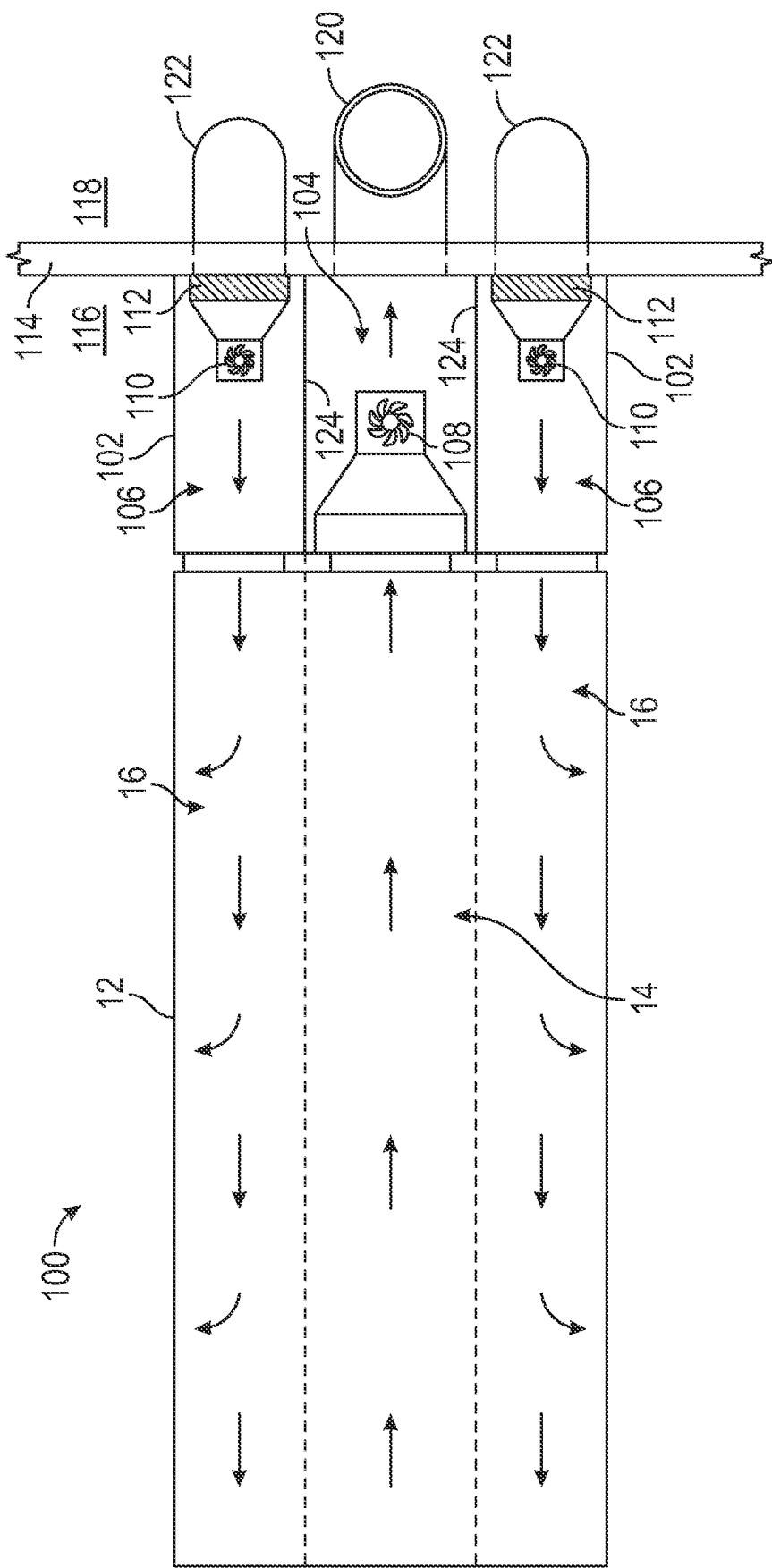
FIG. 11 is a perspective view of a multi-chamber air duct system in accordance with the present disclosure.

FIG. 11 illustrates an alternative embodiment of a system 100 that may be used to draw air from an outdoor space 118 that is separate from the indoor space 116 in which the air duct 12 is disposed and to discharge the outdoor air into the indoor occupied space while simultaneously extracting indoor air and discharging the indoor air into the outdoor space, thereby increasing the ventilation rate by utilizing outdoor air. In this embodiment, the system 100 comprises a fan box 102 that includes an extraction plenum chamber 104 in fluid communication with the negative pressure chamber 14 and a separate discharge plenum chamber 106 in fluid communication with the positive pressure chamber 16. The fan box 102 may be connected to the rigid duct 12 shown in FIG. 1 or to the fabric duct 50 shown in FIG. 5. Thus, in this embodiment, the duct 12, 50 preferably includes two opposing positive pressure chambers 16 and a negative pressure chamber 14 disposed between the positive pressure chambers 16, and, similarly, the fan box 102 preferably includes two opposing discharge plenum chambers 106 and one extraction plenum chamber 104 disposed between the discharge plenum chambers 106. The extraction plenum chamber 104 may be separated from the discharge plenum chambers 106 by internal walls 124 disposed within the interior of the fan box 102, as shown in FIG. 11, so that air cannot move directly between the extraction 104 and discharge 106 plenum chambers.

The extraction plenum chamber 104 of the fan box 102 is also in fluid communication with the outdoor space 118 through an outlet duct 120, which is preferably positioned opposite the negative pressure chamber 14 of the duct 12, 50, as shown in FIG. 11. The discharge plenum chambers 106 are also each in fluid communication with the outdoor space 118 through inlet ducts 122. Air from the indoor space 116 is extracted through the intake openings 20 of the negative pressure chamber 14 by an extraction fan 108 disposed in the extraction plenum chamber 104 and then discharged to the outdoor space 118 through the outlet duct 120. Air from the outdoor space 118 is drawn into each of the discharge plenum chambers 106 from the outdoor space 118 by a discharge fan 110 disposed in each discharge plenum chamber 106 through the inlet ducts 122. The air is then discharged into the indoor space 116 through the discharge openings 22 of the positive pressure chambers 16. Each of the discharge plenum chambers 106 preferably houses a HEPA filter 112 to filter the outdoor air before it is discharged into the indoor space 116. UV-C lamps and/or a bipolar ionizer may optionally be used in addition to or in place of the filters 112. In an alternative embodiment, the two opposing positive pressure chambers 16 may both be in fluid communication with a single discharge plenum chamber 106 utilizing a single discharge fan 110. The internal walls 124 may be arranged to form a single discharge plenum chamber 106 and to direct airflow to both positive pressure chambers 16 from the discharge plenum chamber 106.

The fan box 102 may be mounted on a wall 114 separating the indoor space 116 utilized by occupants from the outdoor space 118 from which outdoor air is directed into the indoor space 116 to minimize the length of the outlet duct 120 and inlet ducts 122. The outlet duct 120 and inlet ducts 122 may pass through the wall 114 and terminate at open ends directly on the opposite side of the wall 114 in the outdoor space 118. In a preferred embodiment, the open end of the outlet duct 120 may face upwardly, and the open ends of the inlet ducts 122 may face downwardly. This configuration keeps the open ends of the inlet 122 and outlet 120 ducts sufficiently distant from each other so that air discharged by the outlet duct 120 is not immediately drawn in by the inlet ducts 122. The upwardly facing open end of the outlet duct 120 may have a cover to prevent rainwater from entering the outlet duct 120.

It is understood that versions of the present disclosure may come in different forms and embodiments. Additionally, it is understood that one of skill in the art would appreciate these various forms and embodiments as falling within the scope of the invention as disclosed herein.

What is claimed is:

1. A system comprising:
an elongated air duct having a first end and an opposing second end, wherein the air duct is installed within an indoor space, wherein the air duct includes a negative pressure chamber and a positive pressure chamber each disposed within the air duct, wherein a wall of the negative pressure chamber has a plurality of intake openings through which the negative pressure chamber is in fluid communication with the indoor space in which the air duct is installed, wherein a wall of the positive pressure chamber has a plurality of discharge openings through which the positive pressure chamber is in fluid communication with the indoor space;
a plenum chamber connected to the first end of the air duct, wherein the plenum chamber defines an enclosed space, wherein the negative pressure chamber and the positive pressure chamber are each in fluid communication with the plenum chamber, wherein the plurality of intake openings and the plurality of discharge openings are distributed along substantially all of a length of the air duct extending between the first end and the second end of the air duct; and a fan configured to draw indoor air from the indoor space into the plenum chamber through the intake openings and the negative pressure chamber, wherein the fan is further configured to discharge the indoor air drawn into the plenum chamber from the plenum chamber back into the indoor space through the positive pressure chamber and the discharge openings.

2. The system of claim 1, wherein the system further comprises an air filter disposed within the plenum chamber, wherein the indoor air drawn into the plenum chamber from the indoor space passes through the air filter, and wherein the filter removes contaminants from the indoor air.

3. The system of claim 1, wherein the system further comprises a UV light disposed within the plenum chamber, wherein the indoor air drawn into the plenum chamber from the indoor space passes through light emitted by the UV light.

4. The system of claim 1, wherein the system further comprises a bipolar ionizer disposed within the plenum chamber.

5. The system of claim 1, wherein the air duct has a rectangular cross-sectional shape, wherein the intake openings are disposed on a bottom wall of the air duct and the discharge openings are disposed on a side wall of the air duct.

6. The system of claim 1, wherein the air duct has a rectangular cross-sectional shape, wherein the intake openings are disposed on a bottom wall of the air duct, wherein the air duct includes two opposing positive pressure chambers disposed lengthwise along two opposing side walls of the air duct, wherein the discharge openings are disposed on each of the two side walls of the air duct, and wherein the negative pressure chamber is disposed between the two positive pressure chambers.

7. The system of claim 1, wherein the second end of the air duct is closed.

8. The system of claim 1, wherein the plenum chamber has internal walls configured to direct air flow from the negative pressure chamber into the positive pressure chamber.

9. The system of claim 1, wherein the air duct is made of pliable fabric.

10. The system of claim 9, wherein the system further comprises four elongated tracks each having a longitudinal groove and four elongated rods, wherein each rod is retained longitudinally within the groove of one respective track, wherein the air duct has a rectangular cross-sectional shape having four corners, wherein each corner is longitudinally secured to one respective rod by a loop attached to the air duct at one corner of the air duct and extending longitudinally along a length of the corner, wherein the loop is positioned longitudinally around one respective rod, and wherein the four tracks are retained in a rectangular relation by horizontal and vertical spacers attached to each of the tracks.

11. A system comprising:

an elongated air duct having a first end and an opposing second end, wherein the air duct is installed within an indoor space, wherein the air duct has a bottom wall, a top wall, and two opposing side walls each extending between the first end and the second end of the air duct, wherein the air duct includes two opposing positive pressure chambers each disposed within the air duct lengthwise along one of the two respective opposing side walls of the air duct and a negative pressure chamber disposed within the air duct between the two positive pressure chambers, wherein the bottom wall of the air duct has a plurality of intake openings through which the negative pressure chamber is in fluid communication with the indoor space in which the air duct is installed, wherein each of the side walls of the air duct has a plurality of discharge openings through which the opposing positive pressure chambers are each in fluid communication with the indoor space;

a plenum chamber connected to the first end of the air duct, wherein the plenum chamber defines an enclosed space, wherein the plenum chamber is in fluid communication with the negative pressure chamber and with each of the positive pressure chambers, wherein the plurality of intake openings and the plurality of discharge openings are distributed along substantially all of a length of the air duct extending between the first end and the second end of the air duct; and a fan disposed within the plenum chamber, wherein the fan, when activated, draws indoor air into the plenum chamber from the indoor space through the intake openings and the negative pressure chamber, and wherein the fan, when activated, discharges the indoor air drawn into the plenum chamber from the plenum chamber back into the indoor space through the opposing positive pressure chambers and the discharge openings.

12. The system of claim 11, further comprising an air filter disposed within the plenum chamber, wherein the indoor air drawn into the plenum chamber from the indoor space passes through the air filter, and wherein the filter removes contaminants from the indoor air.

13. The system of claim 11, further comprising a UV light disposed within the plenum chamber, wherein the indoor air drawn into the plenum chamber from the indoor space passes through light emitted by the UV light.

14. The system of claim 11, further comprising a bipolar ionizer disposed within the plenum chamber.

15. The system of claim 11, wherein the air duct is made of pliable fabric.

16. The system of claim 15, wherein the system further comprises four elongated tracks each having a longitudinal groove and four elongated rods, wherein each rod is retained longitudinally within the groove of one respective track, wherein the air duct has a rectangular cross-sectional shape having four corners, wherein each corner is longitudinally secured to one respective rod by a loop attached to the air duct at one corner of the air duct and extending longitudinally along a length of the corner, wherein the loop is positioned longitudinally around one respective rod, and wherein the four tracks are retained in a rectangular relation by horizontal and vertical spacers attached to each of the tracks.

17. The system of claim 1, wherein the air duct is disposed in a generally horizontal position and in a position that is elevated above a floor of the indoor space.

18. The system of claim 1, wherein the negative pressure chamber and the positive pressure chamber are not directly in fluid communication with each other.

19. The system of claim 1, wherein the system is configured to extract the indoor air from the indoor space along substantially all of the length of the air duct extending between the first end and the second end of the air duct into the negative pressure chamber and to discharge the extracted indoor air from the positive pressure chamber along substantially all of the length of the air duct extending between the first end and the second end of the air duct.

\* \* \* \* \*